(12) United States Patent
Clement et al.

(10) Patent No.: US 6,443,946 B2
(45) Date of Patent: *Sep. 3, 2002

(54) APPARATUS FOR WRINKLE REMOVAL

(75) Inventors: Robert Marc Clement, West Glamorgan (GB); Michael Kiernan, West Glamorgan (GB)

(73) Assignee: ICN Photonics Limited, Llanelli (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/263,422

(22) Filed: Mar. 5, 1999

Related U.S. Application Data

(63) Continuation-in-part of application No. 08/919,472, filed on Aug. 28, 1997, now Pat. No. 5,983,900.

(30) Foreign Application Priority Data

Aug. 29, 1996 (GB) .............................................. 9618051

(51) Int. Cl.[7] .............................................. A61B 18/18
(52) U.S. Cl. .............................................. 606/9; 607/89
(58) Field of Search .............................. 606/2, 3, 9–10, 606/13, 17; 607/89

(56) References Cited

U.S. PATENT DOCUMENTS

| | | | | |
|---|---|---|---|---|
| 4,643,877 A | * | 2/1987 | Opitz et al. | 422/68 |
| 4,829,262 A | * | 5/1989 | Furumoto | 330/4.3 |
| 5,272,716 A | * | 12/1993 | Soltz et al. | 372/109 |
| 5,312,395 A | | 5/1994 | Tan et al. | |
| 5,320,618 A | * | 6/1994 | Gustafsson | 606/9 |
| 5,602,948 A | * | 2/1997 | Currie | 585/33 |
| 5,616,140 A | * | 4/1997 | Prescott | 606/10 |
| 5,624,435 A | * | 4/1997 | Furumoto et al. | 606/10 |
| 5,658,323 A | * | 8/1997 | Miller | 607/89 |
| 5,707,403 A | * | 1/1998 | Grove et al. | 607/89 |
| 5,749,868 A | * | 5/1998 | Furumoto | 606/9 |
| 5,759,200 A | * | 6/1998 | Azar | 607/89 |
| 5,814,040 A | * | 9/1998 | Nelson et al. | 606/9 |

FOREIGN PATENT DOCUMENTS

| | | |
|---|---|---|
| CA | 2198826 | 8/1998 |
| EP | 0763371 A2 | 3/1997 |
| WO | WO 97/28752 | 8/1997 |

OTHER PUBLICATIONS

The Laser Focus World Buyers Guide 1996, p. 113.*

Laser Focus World Buyers Guide, p. 50.*

* cited by examiner

Primary Examiner—Roy D. Gibson
(74) Attorney, Agent, or Firm—Rutan & Tucker, LLP

(57) ABSTRACT

Wrinkles are cosmetically removed from a superficial area of mammalian skin tissue having an epidermal layer, a basal layer, and a dermal layer, by irradiating the dermal layer through the basal layer, the irradiation being selected to be absorbed by a chromophore in the dermal layer such that collagen present in the dermal layer is heated, while the basal layer remains intact so as to substantially inhibit contact of the dermal layer with ambient air.

11 Claims, 2 Drawing Sheets

APPARATUS FOR WRINKLE REMOVAL

This is a Continuation In Part of U.S. patent application Ser. No. 08/919,472 Filed on Aug. 28, 1997, now U.S. Pat. No. 5,983,900.

BACKGROUND OF THE INVENTION

The present invention relates to a method of reducing wrinkles from a superficial area of mammalian skin tissue, and apparatus therefor.

The application of laser technology in healthcare is well known, and the use of lasers in medical applications has been studied extensively since the early 1960's. In recent years an increasing interest has been shown in cosmetic applications. Two such cosmetic applications are skin resurfacing and wrinkle removal; in this field lasers can be used as an alternative to surgical facelifts.

There is a distinct difference between wrinkle removal and skin resurfacing. Skin resurfacing is where laser energy vaporizes thin layers of the epidermis without breaking through the basal layer into the dermis. This is essentially a superficial process primarily used to give the skin a "fresher" appearance. However, wrinkle removal as a more aggressive technique where tissue is removed layer by layer, invading the dermis and effectively inducing a second degree burn. Heat is deposited in the dermis shrinking the collagen and tightening the skin.

In young skin, the collagen just beneath the surface of the skin forms an organized lattice with good elasticity and flexibility. During aging, the collagen changes its structure impacting negatively on the cosmetic appearance of the skin. Several techniques have been developed to induce a "controlled injury" to the dermis in an attempt to generate rejuvenation of the collagen structure returning the skin to an earlier cosmetic appearance. During the 1990's a laser approach to wrinkle removal has been introduced.

For known wrinkle removal techniques, the wavelength is chosen so that the laser energy is highly absorbed in water, the current lasers of choice being the $CO_2$ laser at 10.6 $\mu$m wavelength and the Erbium YAG laser at 2.94 $\mu$m wavelength. In this non-selective process, pulses of laser energy are applied to the skin surface, each pulse vaporizing a layer of tissue between 30 $\mu$m to 60 $\mu$m in thickness. Normally, the first pass of the laser removes a thin layer of the epidermis without damaging the basal layer. Successive passes over the same area penetrate into the dermis and heat the collagen. The laser operator sees this thermal build-up "shrink" the skin in "real time", tightening up the skin's appearance. When the desired clinical outcome is achieved, the operator ceases applying laser pulses. It is therefore apparent that the quality of the cosmetic result is highly dependent upon the experience and skill of the operator.

In the case of $CO_2$ laser wrinkle removal, post-treatment supervision of the patient is a necessity. Immediately after treatment, the skin is essentially an open wound requiring dressings in place for 2–10 days. Additionally, topically applied lotions are required for patient comfort and prevention of infection. Post-operative infection is common, primarily due to removal of the natural protective barrier of the skin, with a reported incidence of between 4.5 to 7%.

On average, with $CO_2$ laser wrinkle removal, post-treatment crythema is present for 4–5 months. This compares to 2–3 months following a Chemical Peel. Also, the incidence of side effects is significant, the most common being hyperpigmentation occurring in 30–40% of cases. Higher incidences are reported in darker skin types. A delayed hypopigmentation, which can occur up to a year after the procedure was performed, has recently emerged as a complication of aggressive laser resurfacing. Many of the eminent laser resurfacing surgeons have resorted to less aggressive techniques.

The effects of known procedures is two fold:

(a) the laser induces denaturing of the collagen in the dermis, and the formation of cross links, which results in a tightening effect stretching the skin, reducing or removing the wrinkles (it is thought that the thermal threshold for this effect is a temperature of 70° C.); and (b) the changes to the dermis induce the generation of new collagen which develops using the matrix created by the denatured collagen as a foundation.

The skin-resurfacing and wrinkle removal procedure outlined above is considered by many experts in the field as a significant improvement over previously used surgical methods. The procedure uses the laser's ability to deliver high energy density at the surface of tissue and hence ablate the surface tissue in a well controlled manner. Continuing to remove the tissue, layer by layer is designed to damage the collagen and hence induce wrinkle removal. This second stage of the procedure is primitive; the skin weeps, scabs form and redness of the skin appears for many weeks.

OBJECT OF THE INVENTION

It is therefore the primary object of the present invention to provide a technique for removing wrinkles from a superficial area of mammalian skin tissue without causing secondary burns and other problems associated with traditional wrinkle removal.

SUMMARY OF THE INVENTION

The present invention provides a method of removing wrinkles from a superficial area of mammalian skin tissue. The dermal layer of the tissue is irradiated through the basal layer by radiation selected to be absorbed by a chromophore in the dermal layer such that collagen present in the dermal layer is heated, while the basal layer remains intact so as to substantially inhibit contact of the dermal layer with ambient air.

According to a further aspect, the invention provides apparatus for cosmetic reduction of wrinkles on a superficial area of mammalian skin, the apparatus comprising a radiation delivery system for delivering a radiation beam of predetermined monochromatic wavelength or narrow wavelength bandwidth to the skin, the radiation delivery system including a pulsation system for pulsing the radiation delivered according to a predetermined regime, and an optical arrangement for focussing the beam such that the total radiation energy density delivered to the skin is substantially in the range of 0.5 $J/cm^2$ to 5 $J/cm^2$ per pulse.

The irradiation of the dermal layer in the method according to the invention is tailored to shrink the skin tissue without damage to the dermis (in other words, without causing second degree burns) because the barrier provided by the basal layer remains intact. This is achieved by selecting the required radiation wavelength to match the characteristic absorbtion wavelength of the chromophore whilst being absorbed to an insignificant degree in the epidermis and basal layer. The energy delivered per pulse is also tailored to ensure that ablation does not occur of the target structure, but rather that energy absorbed in the target provides sufficient heating that heat energy diffusing outwards from the target heats the surrounding tissues to a degree sufficient to thermally induce shrinkage of the surrounding tissue and also stimulate the production of new tissue components such as elastin and collagen.

If the target for the laser has an appropriate chromophore (a substance that absorbs a specific wavelength and transmits or scatters at other wavelengths) then the laser can be used to modify that target selectively within an inhomogeneous volume of tissue. Occasionally, the desired target does not have a suitable chromophore of its own but exists in close proximity to another material which has such a chromophore which can be selectively targeted. Such interaction is called secondary selective interaction.

An artificial chromophore may be introduced into the desired area for wrinkle reduction, or a naturally occurring chromophore may be selected in a preferred embodiment of the technique, the naturally occurring chromophore selected is oxyhemoglobin of the dermal plexus which has wavelength absorbtion peaks at 585 nm and 815 nm, at which wavelengths absorbtion in surrounding tissue components is relatively low.

According to a further aspect, the invention therefore provides apparatus for cosmetic reduction of wrinkles on a superficial area of mammalian skin, the apparatus comprising a radiation delivery system for delivering substantially monochromatic radiation in a bandwidth of substantially 15 nm or less in at least one of the ranges 570 nm to 600 nm and 750 nm to 850 nm, the delivery system including a pulsation system for pulsing the radiation delivered according to a predetermined regime in which the energy density of the substantially monochromatic radiation in the bandwidth of substantially 15 nm or less delivered to the skin is substantially in the range 0.5 J/cm$^2$ to 5 J/cm$^2$ per pulse.

The method according to the invention is non invasive and non-ablative and can readily be performed by non-medical personnel. The total energy delivered per pulse is sufficient to effect the required physical change in the tissue surrounding the target chromophore without causing ablation of the target or other skin components through which the radiation passes.

DESCRIPTION OF PREFERRED EMBODIMENTS

The radiation is preferably substantially monochromatic or at least of a relatively narrow wavelength bandwidth to ensure that it is preferentially selectively absorbed by the target chromophore. A laser source may be used to produce the required wavelength, or a light source, such as an LED may be used with appropriate filtering to permit the selected wavelength (or narrow wavelength band) to pass.

The irradiation may be by means of a source of visible or infra-red radiation (suitably filtered to remove deleterious ultra-violet radiation if necessary). The radiation may be coherent (that is from a laser source). Such a laser source may be, for example, a dye laser, a ruby laser, or a semiconductor laser. If a dye laser is used, its wavelength is preferably such that it is absorbed by oxyhemoglobin (as naturally occurring chromophore present in blood vessels in the dermis).

Alternatively, the superficial area may be treated with an artificial chromophore which is absorbed into the dermal layer. Such an artificial chromophore may be applied to the epidermal layer in the form of a liposome-containing topical formulation. The chromophore may then permeate through the basal layer for delivery to the dermal layer.

When a laser is used, it may be arranged to scan the superficial area and/or to irradiate the dermal layer in pulses. When the laser is in pulsed mode, the pulses typically have duration of 10 μsec to 10 msec (more preferably 200 μsec to 1 msec).

It is sometimes desirable to remove part of the epidermis prior to irradiating the dermal layer according to the invention. Such epidermis removal (known as skin resurfacing) may be effected mechanically (for example by abrasion), or by means of laser radiation. When laser radiation is used for this purpose, it is typically a scanner controlled $CO_2$ laser source.

The energy density per pulse is preferably accurately controlled to ensure that a maximum threshold level (substantially of 5 J/cm$^2$) is not exceeded.

DETAILED DESCRIPTION OF THE DRAWINGS

Figure 1:
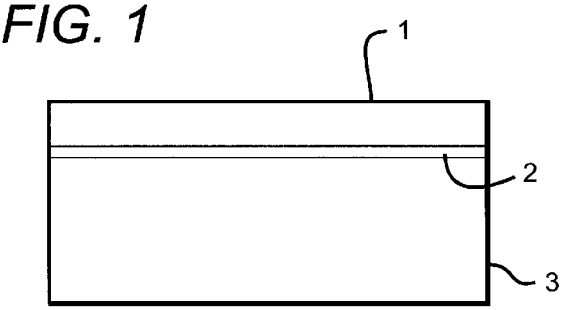
FIG. 1 is a schematic representation of the three outermost layers of mammalian skin tissue.

Referring to FIG. 1, the basic skin structure of mammalian skin tissue comprises three layers, the outermost epidermis 1 which is adjacent to the basal layer 2 and then the dermis 3.

Figure 2:
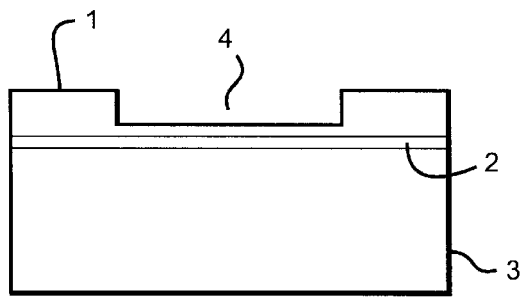
FIG. 2 is a schematic representation of partial removal of the epidermis (skin resurfacing), which is an optional step according to the invention.

Referring to FIG. 2, partial removal of an area 4 of epidermis 1 by means of $CO_2$ laser radiation is known as skin resurfacing. This stage represents the first step of a prior art method but is an optional step according to the invention. Both the basal layer 2 and the dermis 3 are unaffected by the laser radiation.

Figure 3:
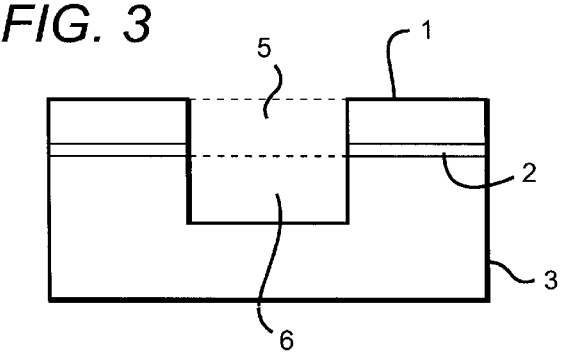
FIG. 3 is a schematic illustration of the result of a prior art method of wrinkle removal, which is surgical because it involves full removal of the epidermis in a selected area and therefore exposure of the dermis and consequent second degree burning.

As shown in FIG. 3, prior art method of wrinkle removal results in complete removal of an area 5 of epidermis 1 and basal layer 2 by repeated exposure to $CO_2$ laser radiation. Partial removal of the dermis 3 also occurs, as represented by 6, leaving the dermis exposed to air. This causes a second degree burn which is slow to heal and a risk of infection.

Figure 4:
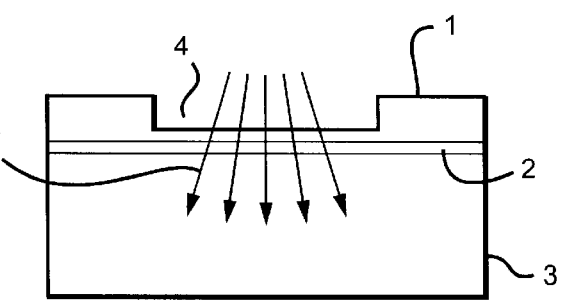
FIG. 4 is a schematic illustration of the result of the method according to the invention, showing that the epidermis is partially intact and the basal layer fully intact.

As shown in FIG. 4, the method of wrinkle removal according to the invention results in partial removal of the epidermis 1 (this is an optional step as described in FIG. 2 above) and the basal layer 2 is left intact, such that the dermis 3 is not exposed to air. Laser radiation 7 is applied to the tissue and selectively absorbed by a chromophore in the dermis 3, heating the collagen and shrinking the skin hence removing the appearance of wrinkles.

Figure 5:
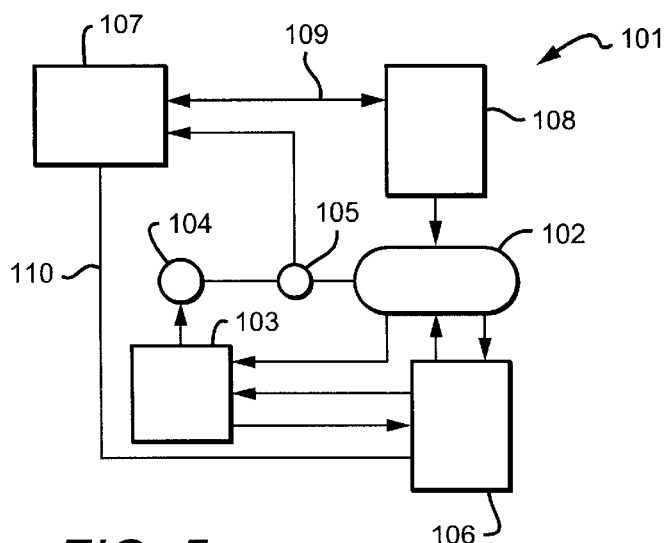
FIG. 5 is a schematic diagram of a first embodiment of wrinkle reduction apparatus according to the invention.

In a preferred embodiment, the target chromophore selected is oxyhemoglobin in the dermis 3 which has absorbtion peaks at approximately 585 nm and 815 nm. The apparatus shown in FIG. 5 comprises a laser radiation delivery system 101 comprising a flashlamp excited pumped dye laser including a laser head 102, dye reservoir 103 and pump 104. A flowmeter 105 regulates dye flow to the laser cavity in the laser head 102 and a cooling system 106 cools the laser head 102 and dye reservoir 103. The system is controlled by a microprocessor controller 107 which operates voltage control of a pulse forming network 108 (including a capacitor and inductor network) which initiates a discharge pulse and consequently a pulsed beam laser output from laser head 102. Voltage control and feedback is provided between the microprocessor controller 107 and pulse forming network 108 via link 109. Temperature monitoring feedback is provided between the cooling system and the controller 107 via link 110.

The laser head operates to output controlled pulses of laser radiation having wavelength in the range 577 nm to 585 nm and a pulse duration in the range 200 $\mu$s to 1 ms. To produce the required wavelength an appropriate laser dye is selected (such as Rhodamine 575 or Pyromethene 590), the concentration of the dye solution is controlled.

Control of the pulse duration for the dye laser arrangement 101 is achieved by accurate control of the energy delivered to the exciting flashlamps in the laser head 102 by tailoring the capacitor and inductor values in the pulse forming network 108.

Figure 7:
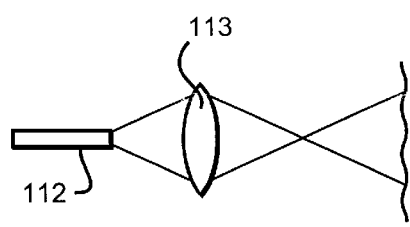
FIG. 7 is a schematic representation of an optical delivery system forming part of apparatus according to the invention; and, FIG. 8 is a graphical representation showing the intensity profile of the radiation delivered using apparatus according to the invention.
Figure 8:
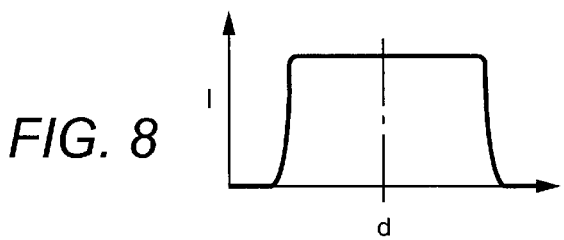

The energy is delivered to the skin surface via a fiberoptic tube 112 (see FIG. 7) and a focussing optical lens arrangement 113 which is configured to focus a light spot on the skin tissue surface so as to have a spot diameter within the range 1 mm to 10 mm, and an intensity distribution across the spot diameter that is substantially uniform (i.e. "a top hat" distribution), as shown in FIG. 8. Providing optics to ensure that the uniform energy distribution results in even heating of the tissue without the occurrence of "hot spots" which could result in tissue damage/oblation.

The radiation parameters are also selected to ensure that the total radiation energy density delivered per pulse falls within the range 0.5 J/cm$^2$ to 5 J/cm$^2$. It is particularly important that the selected upper threshold value (5 J/cm$^2$) is not exceeded significantly as delivery of a higher energy densities of radiation per pulse can result in unwanted effects on the skin (such as ablation and/or other damage).

For the dye laser system 101 of FIG. 1, the energy density of the radiation delivered to the skin is controlled by adjustment of the flashlamp output energy (which in turn controls the laser output energy). The laser output energy in conjunction with the spot site determines the energy density delivered. Accurate control is achieved by control of the dye circulation rate, the dye temperature and the flashlamp output energy. Dye circulation rate is important because repeated pulsing of the same volume of dye, without circulation, reduces the output energy of the laser head 102. Increasing or decreasing the dye temperature has an affect on the energy output of the laser head 102. The flashlamp output energy is controlled by varying the voltage with which the capacitors in the pulse forming network 108 are charged; feedback of the capacitor voltage via link 109 is therefore important.

The energy density required will vary within the specified range from person to person, depending upon skin colour.

Figure 6:
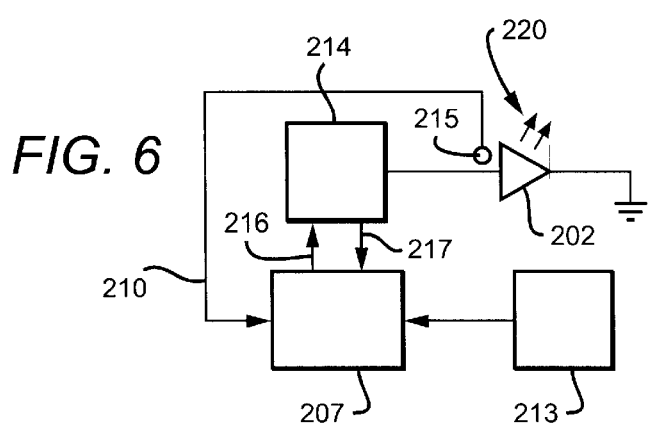
FIG. 6 is a schematic diagram of an alternate embodiment of wrinkle reduction apparatus according to the invention.

Referring to FIG. 6, there is shown an alternative embodiment of apparatus for performance of the invention in which an LED or semiconductor laser device 202 may be utilised to produce the output radiation 220. A user interface 213 enables input into a microprocessor controller 207 which is used to control a power supply unit 214 to ensure that the required current is supplied to the LED or semiconductor laser device 220. A temperature sensor 215 provides temperature feedback via a link 210. Output 216 from controller 207 sets the current supplied by the power supply unit 214 to the device 202; input 217 into the controller 207 provides current monitoring feedback. Control of the pulse duration is achieved by pulsing the current supply from power supply unit 214 to the LED or semiconductor laser device 202.

High intensity LED devices are capable of producing wavelengths corresponding to the 585 nm absorption peak of oxyhaemoglobin. The optical system (including lens 113) may include filters arranged to narrow the band of radiation passing from the LED to the target area of the skin. Where lasers are used, the output may be monochromatic. Alternatively, or in the case where LED's are used, the radiation delivered may be "effectively" monochromatic, or of a relatively narrow band width (typically within a band width of 15 nm or less).

Where a semiconductor laser device is used, the output may correspond to the second (higher) absorption peak (815 nm) for oxyhaemoglobin.

Whilst the invention has been described in relation to delivery of effectively monochromatic radiation (or within specific narrow band widths) at one or other of the oxyhaemoglobin absorption peaks of 585 nm and 815 nm, it is clear that the beneficial effect of the invention can be achieved to a certain degree by using wavelengths relatively close to, but either side, of the respective absorption peaks. Preferred wavelength ranges for operation are 570 nm to 600 nm and 750 nm to 850 nm for targeting oxyhaemoglobin.

Where an artificial chromophore is used, the wavelength (or narrow band of wavelengths) is selected to correspond to a characteristic absorption wavelength of the relevant chromophore. It remains important to ensure that the total energy delivered per pulse is below the threshold damage level (approximately 5 J/cm$^2$).

In the embodiments described, it is important to ensure that there is not excess energy (and therefore heat) build-up in the target, and therefore the inter pulse duration is selected at a level to avoid this situation occurring. It is preferred that the pulse repetition rate is substantially in the range 3 Hz maximum or less.

We claim:

1. A method of producing a significant improvement in an area of skin having a dermal layer and a basal layer, comprising:

providing a source of electromagnetic radiation in a narrow wavelength bandwidth between 570 nm and 600 nm; and irradiating the dermal layer through the basal layer with the electromagnetic radiation, under a set of conditions that produces the significant improvement without significantly damaging the basal layer, wherein the improvement comprises stimulating the skin to produce collagen and the set conditions include providing the electromagnetic radiation as pulses having a pulse duration of between about 10 $\mu$sec and 10 msec, the energy density delivered to the skin being in the range about 0.5 J/cm$^2$ and 5.0 J/cm$^2$ per pulse.

2. The method of claim 1 wherein one of the conditions comprises providing the electromagnetic radiation in a narrow band of wavelengths no greater than 15 nm.

3. The method of claim 2 wherein the narrow band has a peak at about 585 nm.

4. The method of claim 1 wherein one of the conditions comprises providing the electromagnetic radiation as pulses having a pulse width of between about 200 μsec and 1 msec.

5. The method of claim 1 wherein the skin further comprises an epidermal layer, and the epidermis layer is not noticeably heated during the step of irradiating.

6. The method of claim 1 further comprising finding a cosmetic condition in the area of skin, and selectively applying the electromagnetic radiation to the area.

7. The method of claim 6 wherein the cosmetic condition comprises a wrinkle.

8. The method of claim 1 wherein the dermal layer further comprises collagen, and the improvement comprises denaturing the collagen.

9. The method of claim 1 wherein the conditions comprise:

providing the electromagnetic radiation in a narrow band of wavelengths no greater than 15 nm that includes a wavelength between 570 nm and 600 nm;

providing the electromagnetic radiation as pulses having a pulse width of between about 200 μsec and 1 msec, and a total pulse energy of between about 0.5 J/cm$^2$ and 5.0 J/cm$^2$.

10. The method of claim 9 wherein the narrow band has a peak at about 585 nm.

11. The method of claim 9 further comprising using the electromagnetic radiation to treat a wrinkle.

* * * * *